(12) United States Patent
Havens et al.

(10) Patent No.: US 8,203,124 B2
(45) Date of Patent: Jun. 19, 2012

(54) STERILIZATION APPARATUS

(75) Inventors: William H. Havens, Syracuse, NY (US); Robert J. Hennick, Cayuga, NY (US)

(73) Assignee: Hand Held Products, Inc., Skaneateles Falls, NY (US)

( * ) Notice: Subject to any disclaimer, the term of this patent is extended or adjusted under 35 U.S.C. 154(b) by 1059 days.

(21) Appl. No.: 11/796,612

(22) Filed: Apr. 27, 2007

(65) Prior Publication Data
US 2008/0265179 A1   Oct. 30, 2008

(51) Int. Cl.
*A61L 2/10* (2006.01)
(52) U.S. Cl. ..................................... 250/455.11; 422/24
(58) Field of Classification Search ............ 250/455.11, 250/454.11; 422/22, 24, 186.3
See application file for complete search history.

(56) References Cited

U.S. PATENT DOCUMENTS

| | | | |
|---|---|---|---|
| 5,151,135 A | 9/1992 | Magee et al. | |
| 5,195,445 A * | 3/1993 | Riddles et al. | 114/201 R |
| 5,547,635 A | 8/1996 | Duthie, Jr. | |
| 5,919,422 A * | 7/1999 | Yamanaka et al. | 422/121 |
| 6,039,928 A | 3/2000 | Roberts | |
| 6,096,264 A * | 8/2000 | Peifer | 422/1 |
| 6,458,331 B1 | 10/2002 | Roberts | |
| 6,490,351 B1 | 12/2002 | Roberts | |
| 6,849,233 B2 * | 2/2005 | Bushnell et al. | 422/24 |
| 7,372,044 B2 * | 5/2008 | Ross | 250/455.11 |
| 2002/0015662 A1 * | 2/2002 | Hlavinka | 422/24 |
| 2005/0256554 A1 | 11/2005 | Malak | |
| 2006/0008400 A1 * | 1/2006 | Gutman | 422/292 |
| 2006/0216193 A1 | 9/2006 | Johnson et al. | |
| 2006/0261285 A1 | 11/2006 | Broerman | |
| 2007/0102280 A1 * | 5/2007 | Hunter et al. | 204/157.15 |

(Continued)

FOREIGN PATENT DOCUMENTS

EP   EP1905343   4/2008

(Continued)

OTHER PUBLICATIONS

Patent Cooperation Treaty International Searching Authority, PCT/ISA/220 Notification of Transmittal of the International Search Report and The Written Opinion of the International Searching Authority, or the Declaration, dated Aug. 8, 2008 (2 pgs.).

(Continued)

*Primary Examiner* — Kiet T Nguyen
(74) *Attorney, Agent, or Firm* — Heslin Rothenberg Farley & Mesiti PC

(57) ABSTRACT

Embodiments of a sterilization apparatus and methods of using a sterilization system are disclosed in the present application. The sterilization apparatus can take the form of a sterilization chamber comprising a top wall, a bottom wall, end walls and side walls which define the interior of the chamber. Throughout the interior of the chamber, multiple ultraviolet light emitting diodes (UVLEDs) irradiate energy at wavelengths for destroying pathogenic substances and achieving an efficient level of sterilization. A UV transparent plate located within the interior of the chamber can support one or more target devices, and can be proportionally sized to accommodate placement of a target device for the simultaneous and uniform distribution of UV sterilizing energy to the surfaces of a target. The sterilization chamber can provide the necessary decontamination and sterilization measures to effectively eliminate any residual biological contaminants on the exposed or hard-to-reach crevices or features of a medical device. Furthermore, one or more interior surfaces of the chamber may comprise a UV reflective material for distributing UV radiation upon substantially all surfaces of a target.

18 Claims, 3 Drawing Sheets

FOREIGN PATENT DOCUMENTS

| GB | 2427113 | 12/2006 |
|---|---|---|
| WO | WO2006/022466 | 3/2006 |
| WO | WO2006/131720 | 12/2006 |
| WO | WO2007/010657 | 1/2007 |

OTHER PUBLICATIONS

Patent Cooperation Treaty, PCT/ISA/210 International Search Report dated Aug. 8, 2008 (4 pgs.).

Patent Cooperation Treaty, International Searching Authority, PCT/ISA/237 Written Opinion of the International Searching Authority dated Aug. 8, 2008, (7 pgs.).

Roberto S. Benson, "Use of Radiation in Biomaterials Science", *Nuclear Instruments and Methods in Physics Research Section B: Beam Interactions with Materials and Atoms* vol. 191, Issues 1-4, May 2002, pp. 752-757 The University of Tennessee, Material Science and Engineering, 427-C Dougherty, Knoxville, TN, 37996-2200, 1 page.

"6 Sterilization and Disinfection in the Laboratory", McGill Laboratory Biosafety Manual-Second Edition, 1997, URL: http://www.hoslink.com/sterilisation.htm, 9 pages.

Saint-Gobain Quartz, "Vitreosil® UV/VIS Optical Fused Quartz", URL: http://www.quartz.saint-gobain.com/Media/Documents/S0000000000000001011/Vitreosil%20UV-VIS%20Optical%20Fused%20Quartz.pdf, 2 pages, Aug. 2006.

Ben Ames, IDG News Service, PC World, "Motion Computing Launches Tablet PC for Doctors", URL: http://www.pcworld.com/printable/article/id,129202/printable.html, 1 page, Feb. 20, 2007.

Jacqueline Hewett, "Lasers, Optics and Photonics Resources and News", Optics.org, URL: http://optics.org/cws/article/research/20365, 2 pages, Sep. 29, 2004.

Kensuke Murai and Yasuyuki Miyano, "Sterilization by Pulsed-Laser Irradiation Through Optical Fiber", Japanese Journal of Applied Physics, vol. 45, No. 8A, 2006, pp. 6537-6538, URL: http://jjap.ipap.jp/link?JJAP/45/6537/, 2 pages.

UVP, "UV PCR Cabinets and Workstations for Contamination Free Environments", URL: http://www.uvp.com/UVP/sept2006.html, Sep. 2006, 1 page.

NATO OTAN, NATO Advanced Research Workshop, "UV Solid-State Light Emitters and Detectors—Abstracts", URL: http://www.natoarw-uv.ff.vu.lt, Jun. 17-21, 2003.

\* cited by examiner

STERILIZATION APPARATUS

FIELD OF THE INVENTION

The present invention relates generally to sterilization devices. More particularly this invention relates to an apparatus for decontamination of instrumentation such as portable data terminals as used in the medical setting or clean-room environment.

BACKGROUND OF THE INVENTION

At the present time, existing technology utilizes equipment and instrumentation in the hospital setting and industrial clean-room environment requiring sterilization. Current cleaning methods, however, are not acceptable for decontaminating the various devices that have been implemented in these settings. In particular, data collection devices have become important in tracking vital signs of a patient and their location within the hospital. One such device includes the portable data terminal (PDT) used to communicate real-time information between patient and medical professional. For example, as medical professionals frequently monitor a number of patients in telemetry or triage, the PDT interfaces with multiple users and is exposed to multiple settings where blood, body fluids, dust, debris and pathogenic organisms can contaminate the surface. As PDTs and other electronic instruments become more utilized throughout a clean medical environment, sterilization of the devices becomes essential to sustaining their use in these facilities.

Current cleaning methods such as using warm water and mild detergents to minimize any damage to the housing or user interface of the device do not adequately sterilize the equipment. Thus, microorganisms may be shielded within air bubbles or under dirt, grease, oil, or clumps of microorganisms. Furthermore, cellular proteins and other byproducts may reduce the efficacy of some liquid germicides.

Similarly, any subsequent chemical treatments to clean the device may cause damage to both internal and external components of the device, potentially interfering with the necessary communications between a patient and the medical professional. Typically, disinfecting solvents such as benzenes and alcohols (with a low residue), chlorination and alternative disinfectants are used to clean a PDT following the pre-washing step. These chemicals have been known to disintegrate the plastic composition of the housing and user interface of a PDT. This further creates the potential for damage to the optical electronics that are indirectly exposed to such treatments through crevices in the manufactured PDT. Unfortunately, the chemicals that may disinfect may not necessarily sterilize the device from contamination by microorganisms and pathogens.

Although hospitals use chemicals and high temperature steam (i.e. autoclaving) for sterilizing surgical instruments, these methods are inappropriate for use with an electronic device or electronic instrumentation. Chemical and steam sterilization are not even practical for the widespread sterilization for common devices. Moist or dry heat and chemical sterilants do not produce desirable levels of sterilization as necessitated by sterile and surgical needs of the medical profession. These current attempts undoubtedly cause damage to the PDT. Alternatively, gamma radiation may be used, as applicable for single-use medical supplies that do not tolerate heat and pressure or chemical treatments, but creates safety hazards for the user. Thus, present measures for sterilizing medical electronic devices have not been successful in providing necessary sterilization without delivering undesirable effects from thermal, chemical or ionizing radiation treatments.

To achieve desirable sterilization results, researchers have looked toward the effects of ultraviolet (UV) radiation. Although the light emitted from UV lamps has proven to be germicidal at about 260 nm wavelengths, and can be used to reduce the number of pathogenic microorganisms on exposed surfaces and in air at about 280 nm wavelengths of the electromagnetic spectrum, the UV lamp light has poor penetrating power. Accumulations of dust, dirt, grease, or clumps of microorganisms shield microorganisms from direct exposure required for the UV lamp light to be lethal. In addition, lamp age and poor maintenance of the UV lamp reduces performance. Furthermore, because UV lamps are typically larger, relative to the size of the object being sterilized, it may be more difficult to develop illumination configurations that do not cause shadows or regions of reduced radiation on the surfaces of multisided objects.

Conventional UV lamps have included low pressure and medium pressure monochromatic and polychromatic mercury vapor arc UV lamps, but do not deliver magnitudes of irradiation as required for inactivation of nucleic acid repair and replication mechanisms, and thus requiring long exposure times. Low pressure lamps, inherently low power devices with a very limited range of disinfection, are not capable of complete microbial decontamination. In addition, these lamps have high output variability. Medium pressure lamps produce a wider UV spectrum and generate levels for sterilization, but are very limited due to their high operating temperatures (400-1000° C.), non-uniform behavior, low electrical efficiency and high cost. ("Disinfection by Ultraviolet Radiation."*Disinfection, Sterilization, and Preservation*. Blatchley, Ernest R. III and Peel, Margaret M., Ed. Seymour S. Block, Philadelphia: Lippincott Williams & Wilkins, Fifth Edition, 2001, p. 828). Luminous efficiency of these lamps is no greater than about 5%, leaving about 95% of the energy lost as heat. Id. The toxicity of mercury also presents a safety concern.

Further advances in engineering mercury vapor arc lamps have led to peak power pulsed UV light (i.e., the Pulsed Xenon Arc Lamp by Xenon Corporation). However, only 45-50% of the input energy is converted to optical energy when operated at optimum conditions. See Xenon Corporation, Chapter 5, SteriPulse Products, p. 19. Collection and redirection of the UV energy is critical to achieving the necessary sterilization effectiveness. Although the pulsed UV light may provide greater sterilization than conventional measures, the system may easily succumb to design errors. Improper or inefficient optical design dissipates heat and reduces optimization of its energy use.

Current needs for decontamination exist in environments requiring sterility. Such needs are present in various industries including: medicine and surgery, food decontamination, medical device and pharmaceutical packaging, sterilization in industrial clean rooms, inactivated vaccine manufacture, air disinfection and water decontamination systems. Although cleaning a data collection device with solvents may potentially remove extraneous substances from the device, this disinfection procedure does not efficiently sterilize the device for use in the sterile setting. Despite various attempts, no biological material may be destroyed at all. Minute crevices and hidden/unexposed surfaces areas in the design of portable data devices limit manual attempts to sufficiently decontaminate the entire device from bacteria, fungi, and various pathogens.

Significant developments have been achieved in the emerging technology of highly efficient light emitting diodes (LEDs). With luminous efficiency at least two times better than incandescent lamps, LEDs are much longer lasting light sources than incandescent lamps. One limitation in developing this technology, however, has been the availability of LEDs in a multitude of spectral ranges/colors. Currently, LEDs in the medical setting have been used in the therapeutic medical treatment of patients including removal of acne and wrinkles, (blue and yellow LEDs) and for the reduction of muscle pain or increased collagen content in the body (red LEDs). Only recently were UVLEDs demonstrated. Limitations still exist, however, in implementing LEDs as broadband sources of illumination from UV to far-infrared radiation. These limitations include the effects of the LEDs' energy efficiency and the difficulty in configuring systems that could potentially damage internal electrical or optical components. Furthermore, direct illumination causes shadows or regions of reduced radiation on the surfaces of three-dimensional objects.

With increasing demands for the sterilization of instrumentation and electronic devices for use in sterile or clean-room environments, there is a need for a system that will efficiently decontaminate and sterilize the surfaces of the devices. Such a system or apparatus will be capable of inactivating any residual microorganisms on the surfaces of a PDT for complete biological decontamination. The sterile apparatus will provide a system for sterilizing hard to clean data devices to effectively eliminate the transfer of pathogenic organisms between patients and minimize the spread of germs and disease. In addition, the apparatus will be capable of being sterilized without causing damage to internal or external components of the device. Accordingly, sterilization of the data device in between shifts of employees, such as changeover of nursing or medical staff, or in between interactions with patients will be beneficial to maintaining the sterility of the hospital setting. The apparatus should therefore be resilient to repeated sterilization effects and remain fully functional before and after sterilization.

Furthermore, a system designed for high throughput applications in the hospital setting would greatly benefit both patients' and medical professionals' safety concerns. The development of energy resources will also contribute to the design of a system for use in sterilizing medical instrumentation and electronic data devices.

SUMMARY OF THE INVENTION

The system of the present invention can be efficiently configured and designed to provide sterilization of the surfaces of a device by effectively removing substantially all contaminants including pathogenic substances. An apparatus for sterilizing surfaces of target devices from contamination by microorganisms comprises one or more walls which define an interior for containing UV radiation such that the interior can be proportionally sized to enclose a target device; a source of radiation comprising a plurality of LEDs such that the LEDs positioned can be positioned in combination with one or more walls; a power supply providing energy to the LEDs such that the LEDs emit UV radiation into the interior; and a holder or support enclosed by the one or more walls so that the plurality of UVLEDs in combination with the support expose substantially all surface areas of the target device to UV radiation. An opening or aperture in at least one wall may be present or an entire wall may be capable of opening to allow placement of the target device within the chamber. Where the apparatus is configured to be placed over or surrounding a target area or particular device, no aperture need be present. The support can therefore be suspended or situated for enclosure by the one or more walls so that the UVLEDs and support(s) allow substantially all surfaces of the target device exposure to UV radiation. The chamber so configured allows for the removable placement of the target device to and from the interior of the chamber. A source of radiation having a plurality of ultraviolet light emitting diodes (UVLEDs) for emitting radiation into the interior of the chamber; and a power supply providing energy to the UVLEDs further enables operation of the system. A first wall including a plurality of LEDs and a second wall positioned away from the first wall can include a UV reflective material. More than one wall, such as a second wall, may include a plurality of LEDs. For example, when the first wall comprising the UVLEDs irradiates UV energy, the second UV reflective wall can distribute UV radiation throughout the interior of the chamber.

In one embodiment, the sterilization chamber can be used as an apparatus to sterilize surfaces of a target device, which may include surfaces and features of portable data devices. In one aspect, the sterilization chamber may be utilized and configured to operate where decontamination of any instrument or data instrumentation is desired. Incorporation of such a chamber within the medical field or in clean-room environments can provide benefits where certain levels or degrees of sterilization are required. Therefore, any potentially sterile environment may utilize a sterilization chamber of the present invention and design a system that particularly functions to efficiently sterilize the determined target surface area.

A method of sterilizing a portable data device may also disclosed in the present application. The method comprises enclosing a data device in a sterilization chamber comprising a distribution of UVLEDs where the UV radiation can be sealed within the interior confines of the chamber; and irradiating the surfaces of the data device simultaneously with UV radiation, potentially destroying substantially all biological contaminants that may be present on the data device. Where the data device itself comprises modified manufactured components to prevent UV degradation and chemical damage, the device may be cleansed prior to the step of irradiating.

The system of the present invention for sterilizing a portable data terminal can therefore comprise a portable data terminal which has a housing and a plurality of features; a holder transmissive to UV radiation and capable of supporting the portable data terminal; and one or more walls enclosing the portable data terminal and forming a closed compartment such that at least one wall having a first surface integrating an array of LEDs for emitting UV radiation upon the portable data terminal and the array of LEDs have a power source. A second surface comprising a UV reflective material can disperse UV radiation throughout the closed compartment. The second surface as part of at least one wall or included in a second wall may be in conjunction with the UVLEDs or without the UVLEDs.

DETAILED DESCRIPTION OF THE INVENTION

In the following detailed description, for purposes of explanation and not limitation, exemplary embodiments disclosing specific details are set forth in order to provide a thorough understanding of the present invention. It will be apparent, however, to one having ordinary skill in the art that the present invention may be practiced in other embodiments that depart from the specific details disclosed herein. In other instances, detailed description of well-known devices and methods may be omitted so as not to obscure the description of the present invention.

Figure 1:
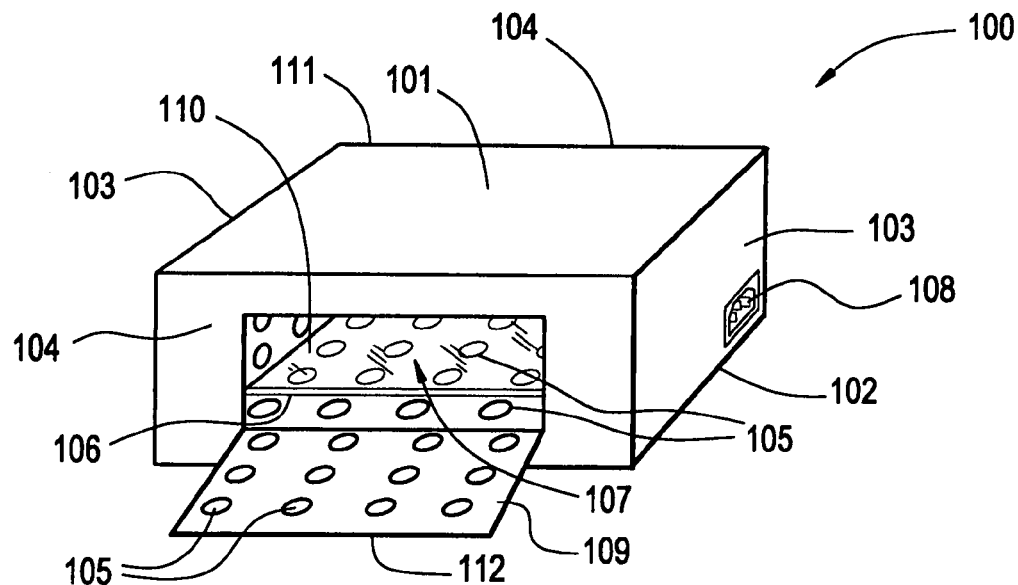
FIG. 1 is a perspective external view of an illustrative embodiment of the apparatus.

An external view of one embodiment of an apparatus is illustrated in FIG. 1. As illustrated, the apparatus 100 can take the form of a sterilization chamber 100. The sterilization chamber 100 comprises a top wall 101, a bottom wall 102, end walls 103 and side walls 104 which define the interior 110 of the chamber. Disposed within the chamber 100 are individual ultraviolet light emitting diodes (UVLEDs) 105 for irradiating energy at wavelengths of about 280 nm. At this wavelength, the irradiance level has the potential to destroy biological materials to achieve an efficient level of sterilization. Throughout the interior of the chamber 100, multiple UVLEDs 105 are arranged on the top wall 101, bottom wall 102, end walls 103 and side walls 104. Since distributed configurations of UVLEDs irradiate a target device most efficiently, the UVLEDs illustrated are in rows that irradiate multiple surfaces of a target consistently. A power supply 108 provides energy to the UVLEDs 105 which may be an internal supply of energy such as a battery or may be a separate extension for connected to an external power source.

The holder 106 for positioning a target to be sterilized may be depicted as a UV transparent plate 106 located within the interior 110 of the chamber. The UV transparent plate 106 is capable of supporting one or more target devices, but should be proportionally sized to accommodate placement of a target device within the interior 110 of the chamber. In addition, the UV transparent plate 106 will be capable of transmitting enough UV light for the equivalent distribution of UV sterilizing energy to the surfaces of a target. An aperture 107 in a side wall 104 provides access to the holder 106 and is sized to facilitate the placement and removal of a target from the interior 110 of the chamber 100.

As shown in one aspect, the aperture 107 in combination with a hinged door 109 and a seal 112 separates the interior 110 from the exterior compartment body 111, thus containing UV radiation within the interior and preventing any stray UV light from escaping. The door 109 is open in FIG. 1 and illustrates the placement of UVLEDs 105 in the configured pattern of rows to further accommodate the needs for illuminating a target device for uniform sterilization. The door 109 may be any door known in the art to accommodate the design of the aperture 107. The seal 112 may also be any known seal in the art that would prevent UV light from exiting the chamber and serve as a precautionary measure to protect the safety of its user.

In one embodiment of the present invention, the UVLEDs 105 can be developed with an irradiance level in the region of 240 nm-365 nm to effectively sterilize and decontaminate a target such as a medical device from biological contaminants. In particular, the UVLEDs when configured in a particular arrangement to direct irradiation at the target have the potential of sufficiently sterilizing the electronic medical device for use in a sterile hospital setting. As used to communicate vital signs data between patients and medical professionals and to monitor patients throughout a medical facility, these devices can now be more efficiently sterilized after being handled and transferred between various persons, and throughout various areas and rooms of the hospital. The sterilization chamber 100 of the present invention can provide the necessary decontamination and sterilization measures to effectively eliminate any residual biological contaminants on the exposed or hard-to-reach crevices of a medical device. Although the purpose of the invention may serve to effectively eradicate substantially all biological contaminants from a portable target device, the sterilization unit can be used for electronic devices that have previously been difficult to decontaminate to a level of sterilization. The invention, however, is not intended to be limited to use with portable data devices and may be desirable for use in any settings where sterilization is needed or beneficial.

Another aspect of the present invention can include the interior surfaces of the walls 101, 102, 103, 104 of the chamber containing a UV reflective material. For exemplary purposes, and not limitation, the composition of the walls may include a reflective material or the walls can be coated or painted with a UV highly diffuse paint. For example, polished aluminum can be used a wall material because it has a high reflectivity in the UV portion of the spectrum. Under some conditions the reflectivity can exceed 85%. This would further increase the efficiency of the sterilization chamber 100 to irradiate UV energy upon all surfaces of a target simultaneously and uniformly.

UV light systems 105 utilized can be UVLEDs that produce UV radiation in one to three bands: UVA (about 315 nm-400 nm), also known as black light which makes certain pigments fluoresce with little effect on pathogens and no effect on human tissue; UVB (about 280 nm-315 nm) which inactivates a moderate amount of pathogens; and UVC (about 200 nm-280 nm) which is more effective in destroying bacteria, inactivating pathogens by destroying their DNA and RNA. UVLEDs 105 when used in the appropriate distribution for irradiation of specified surface areas of a target meet the needs in the medical field where sterilization measures must destroy, and/or remove pathogenic bacteria, viruses, protozoa, and other parasites.

In one aspect, the UVLEDs may include high UV-B and UV-C exposure in the range of about 240 nm-280 nm. In another aspect, the UVLEDs may have peak emission wavelengths in the range of about 250 nm-365 nm. Currently developed UVLEDs include AlGaN/GaN LED chips from Sensor Electronic Technology, Inc. UVLEDs with peak emission wavelengths ranging from about 260 nm-262 nm could be utilized for their capabilities in maximizing absorption of DNA molecules and micororganisms. In addition, e-coli disinfection in the range of about 275 nm-280 nm has germicidal efficiency similar to the 254 nm mercury lamp. The type of UVLED could therefore depend upon the level or measure of sterilization desired for a particular application, such as where a high degree of sterilization may be required in the medical setting, particularly in operating rooms. Therefore, the sterilization system could include emissions wavelengths between about 240 nm-365 nm, between about 240 nm-280 nm or 270 nm-290 nm, or at about 260 nm-262 nm. The system may optimally target specific pathogens by selecting UVLEDs to a subrange of the broader wavelength spectral range.

The invention, however, is not limited to the medical setting where other industrial settings may desire particular degrees of sterilization or levels of decontamination. Such industrial environments may include clean-rooms in manufacturing facilities, packaging facilities, food and pharmacological plants, or any research and development laboratory facility.

Figure 2:
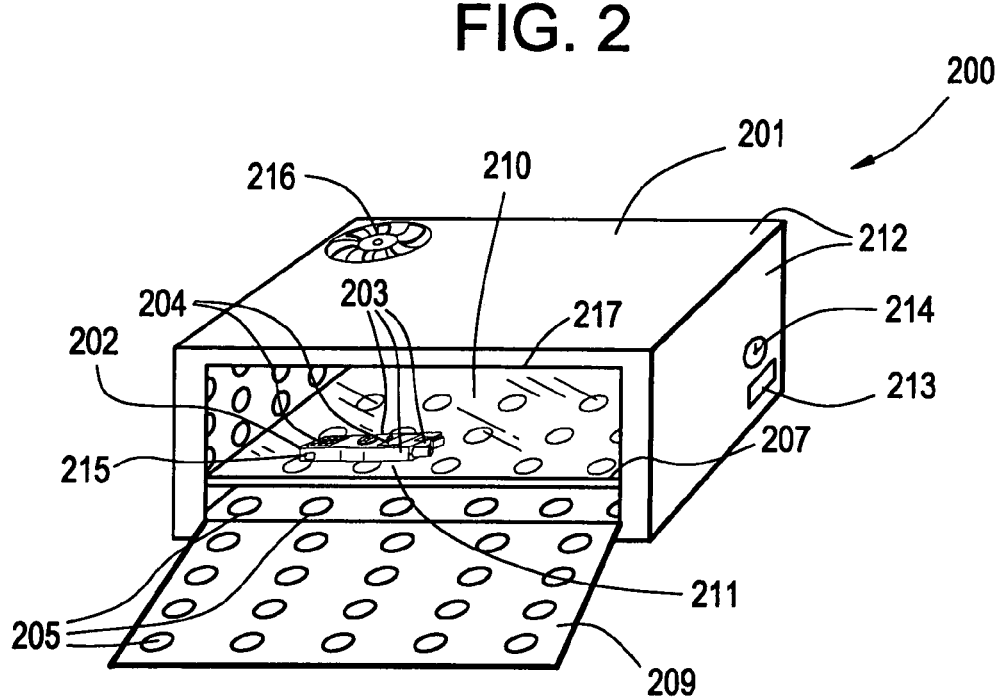
FIG. 2 is a perspective view of an illustrative embodiment of the system.

FIG. 2 illustrates the system 200 including the sterilization apparatus 201 and the data collection device or portable data terminal (PDT) 202 positioned within the interior 210 of the apparatus. UVLEDs 205 in the region of 280 nm that direct radiation upon a surface have the potential of destroying biological material and achieving a sufficient degree of sterilization. The UVLEDs require much less energy than older arc UV sources and can be better directed than the alternate fluorescent type lamps. Using a number of UVLEDs 205, it is possible to structure the box-like chamber 201 containing rows of UVLEDs 205 directed at the peripheral surfaces 203 of a three-dimensional PDT 202. In one aspect, 100 UVLEDs are distributed throughout the chamber 201 on the inner portions of walls 212 of the chamber 201. The UVLEDs operate at a forward current of approximately 30 mA such that the surface area illuminated by each LED 205 is about 4 cm$^2$, thereby accomplishing the desired sterilization of substantially all surfaces of a PDT with a combined surface area of 394 cm$^2$ within approximately 42 seconds. Although LEDs are often tested at a current of about 20 mA, here, the LEDs operate at a slightly increased current of about 30 mA. The output, however, is approximately proportional to the current.

Therefore, depending on the target surface area, the sterilizer can be configured with the desired number of LEDs to effectively sterilize the preferred target. The calculation for determining the number of UVLEDs that would sufficiently sanitize all surfaces of the PDT simultaneously thus takes into the account the particular UVLED emitters that are utilized. For exemplary purposes and not limitation, UVLEDs emitters with an output of approximately 0.5 mW at 20 mA and can be operated at 30 mA:

Step 1: Determine the surface area of the target PDT device 202. A typical hand held PDT as used in the medical setting is about 3.5 cm×6.7 cm×17 cm:

Total Surface Area=394 cm$^2$

Step 2: Determine the output of the particular UVLED emitters. UVLEDs with an output of approximately 0.5 mW at 20 mA can be operated at 30 mA:

3/2*0.5 mW=0.75 mW

Step 3: Determine irradiance: When projected onto an area of 2 cm by 2 cm (4 cm$^2$), an irradiance (I) per UVLED can be determined.

$I$=0.75 mW/4 cm$^2$=0.19 mW/cm$^2$

Step 4: Determine the number of UVLEDs that would sterilize substantially all surface areas of the target device 202. A UVLED which emits a wavelength at 280 nm for the system would be desirable in a configuration utilizing a number (N) of LEDs:

$N$=Target Surface Area/4 cm$^2$=394 cm$^2$/4 cm$^2$=99.5=99 LEDs

Step 5: Position the UVLEDs for irradiating all surfaces of the target device. The 99 LEDs could then be positioned about the internal perimeter of walls 212 of the device 200. In order to illuminate the bottom surface 211 of the PDT 202, the PDT is placed on a plate of UV transparent material 207 such as UV/V is fused quartz.

Step 6: Determine the duration of exposure. UV radiation at about 270-280 nm can be used to sterilize objects. The energy (E) required for 90% inactivation of DNA containing microorganisms, most viruses and bacteria is 8 mW-sec/cm$^2$ objects (U.S. Pat. No. 5,547,635). If the irradiance is 0.19 mW/cm$^2$, the exposure time is then:

Exposure Time $(T)$ =

$E/I$ = 8.0 mW – sec/cm$^2$ * 1/0.19 mW/cm$^2$ = 42 seconds

Construction of the sterilization chamber with approximately 100 LEDs spaced to illuminate each side of the PDT evenly can then be designed. Although the calculation determines the number N to be 99 LEDs, more than 99 LEDs may be utilized to be effective for that particular target surface area. For exemplary purposes and not limitation, exceeding the calculated number N may or may not be more efficient depending on the developments in LED technology. When determining the positioning of the LEDs, it is possible to incorporate the UV transparent glass, such as UV/v is optical fused quartz, anywhere within the interior of the chamber. In addition, the layer of UV transmissive material will be easily accessed to insert and remove a PDT from the chamber. As illustrated in FIG. 1 and FIG. 2, the LEDs 105, 205 (respectively) are included on a surface of the hinged door 209. The hinged door seals off the compartment 201 around the aperture periphery 217 when the door 209 is closed. In addition, the UVLEDs may be incorporated with the sealed compartment to illuminate the surfaces of the PDT more uniformly. Any known seal composed of flexible material, such as rubber or otherwise, may be arranged around the aperture periphery 217 to create a tighter seal.

The closed compartment can substantially eliminate stray energy from escaping the interior, especially where the purpose would be to scatter UV radiation upon multiple surfaces. Such circumstances may exist when the inside surface of the chamber is coated with white paint, or any coating that does not absorb UV light. For example, optically diffuse paint specifically designed for high UV reflectivity may be used in combination with the UVLEDs to simultaneously irradiate the target surfaces of a PDT, thereby substantially and uniformly sterilizing the PDT. Paints or coatings permit various materials to be utilized in the construction of the chamber where the coatings are applicable to a surface of the manufactured chamber. Any UV reflective material, however, may be incorporated in the composition of the chamber wall or surface during manufacture or assembly. As discussed above, polished aluminum could be utilized as a surface material because of its high reflectivity.

In one embodiment, the chamber 201 can be made from metal. A ceramic mounting sheet or other materials that serve as heat sinks to remove heat from the LEDs may also be utilized in the construction of the chamber 201. Heat may also be dispersed with the placement of a fan 216 in one of the walls 212 of the chamber 201. In another aspect, the chamber may be enclosed in a plastic facade or other material to aesthetically modify the chamber or enable easier cleaning. In addition, the UV transparent plate holder 207 preferably is composed of quartz or optical fused quartz. Other UV transparent materials such as more cost efficient quartz-like material or alternative UV transmissive materials may be utilized. Other features may also be added so that shadows are minimized on the surfaces 203 of the device depending on the distribution of individual UVLEDs 205.

Figure 5:
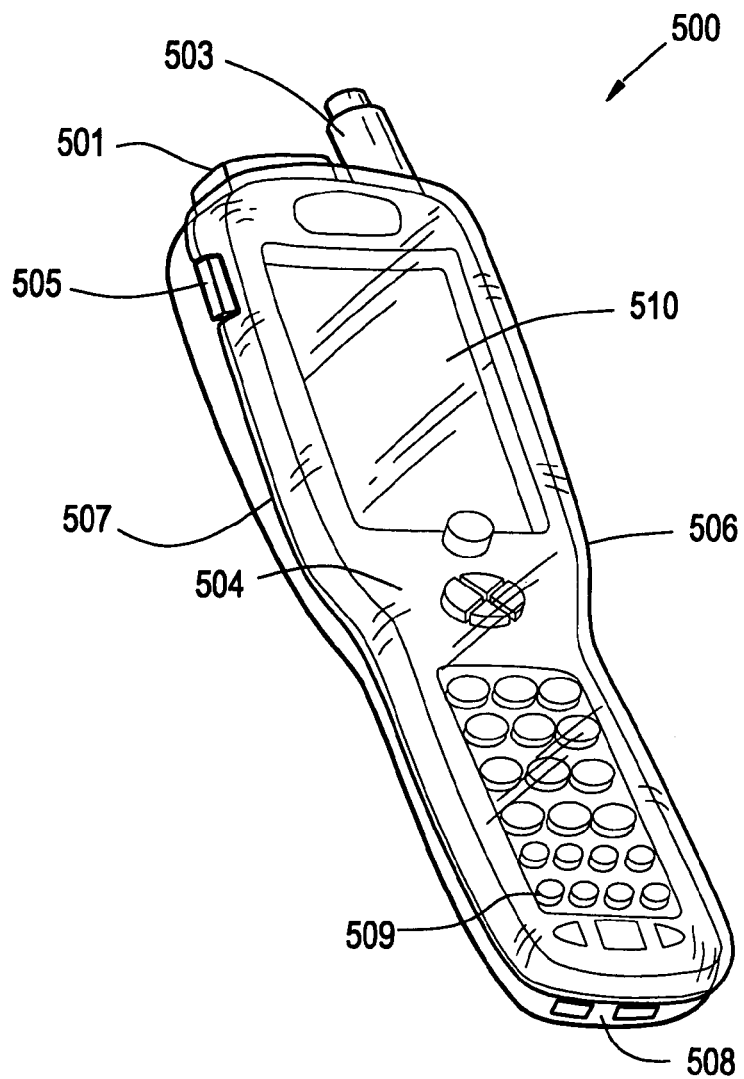
FIG. 5 illustrates a perspective view of one embodiment of a portable data terminal (PDT).
Figure 5A:
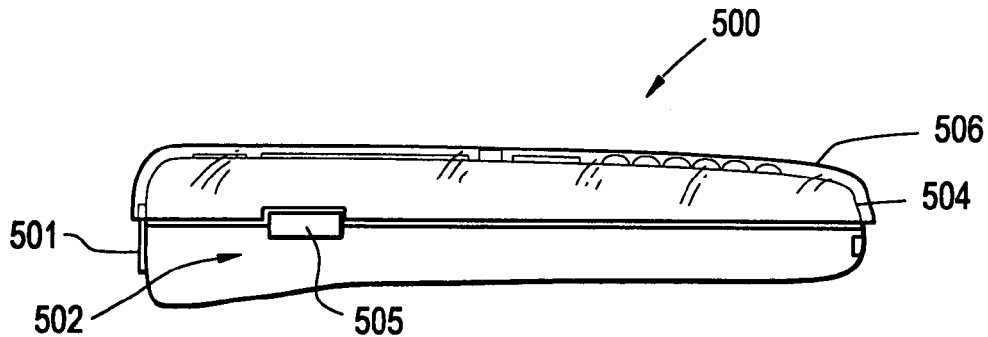
FIG. 5A is an exploded perspective side view of the embodiment of FIG. 5.

In another embodiment, the PDT 202 can be manufactured using plastics that have UV inhibitors to prevent physical or chemical degradation, or UV damaging effects, to the PDT's housing material or surfaces 203. Additional modification of the PDT 202 may easily accommodate current procedures in cleansing the surfaces 203 of the electronic device 202 prior to UV sterilization. In one aspect, the internal electronic components of the PDT 202 may be sealed away from external environmental conditions so that water and other solvents can be used to first remove and roughly clean any large accumulations of material such as blood, other fluids or matter of contamination from the unit before exposing it to the UV light. One aspect, as illustrated in FIG. 5, may include the keypads 509 of the PDT as an integral surface with the user interface 204. The keypads 509 may therefore include tactile dome switches 506 such as those produced by Snaptron, Inc. to provide an easy-to-clean surface which may possibly include non-pathogenic plastics and materials that are non-supportive of any biological growth. An exploded view of the PDT in FIG. 5A demonstrates that a dome switch or covering 506 may be separate from the PDT. The covering 506, however, may be composed of any flexible or rigid transmissive material which allows the user interface 204, including the keypads 509 or screen 510, to be easily accessed. The recesses (e.g. the recessed or elevated surfaces in each key of the keypad) that previously trapped debris or allowed substances to leak between the crevices and cracks in the device would be sealed by this design.

In one aspect, a user interface which seals the electronic components of the PDT from external contamination can be made from any UV protected material. To minimize the effects of yellowing, loss of gloss, loss of strength and haze, some options include the addition of UV inhibitors to the plastic or molded parts. As used to mold plastic parts, black carbon particles serve to resist UV degradation. Another option would be to make the housing from a material such as aluminum or magnesium that is not subject to UV attack. Any combination of materials, however, may be utilized such as where a multi-component target device is comprised of an upper Mg housing and a lower bottom plastic housing or any combination or parts.

Further aspects as related to the improved chemical resistance of a PDT device may be advantageous in various other applications of the present invention. The PDT design may include surfaces made from materials that are not easily attacked by solvents. This could be achieved by molding the housing components in a thermoplastic material (ABS, UItem, etc.) and then copper plating the parts. A second plating of nickel or chrome may be applied to prevent oxidation of the copper and improve the cosmetics of the device. All metal parts are another option that could be plated and coated. In another aspect, nylon or epoxy powder may be coated via an electrostatic process over the copper plated plastic component.

Yet other options may exist to incorporate microbial resistance to bacteria in the manufacture of the PDT device. One option would be to apply a powder coating to a copper plated plastic component that has an anti-microbial agent such as AgION. Silver is naturally anti-microbial and would be another possibility for manufacture of the PDT device. Powder coating is also versatile in providing cosmetic colors and texture variations. Further, another possibility may be to apply the microbial as a coating to the thermoplastic component or incorporate the microbial within the composition of the molded thermoplastic part. No added chemical resistance, however, may be achieved in this scenario.

In another aspect of the present invention, a microcontroller 213 can be used to control the functionality of the LEDs. For exemplary purposes and not limitation, the system 200 can include a timer 214, alone or in combination with the microcontroller 213, to ensure that the sterilization device 201 functions for the proper amount of time. Also, for reasons of eye and skin safety, the UVLEDs 205 should not be activated when the access door 209 is open. The system 200 may therefore also include a UV sensor 215 with each individual PDT 202 to determine the total amount of UV energy incident on the surfaces 203 of the PDT 202. The sensor 215, approximately 5 mm in diameter, or sized for the particular device, can automatically record each time the PDT 202 is decontaminated; the decontamination record is then accessed through software on the units of the PDT's user interface 204 (the interface of which includes the screen and keypad). The sensor, however, is not limited by the description disclosed and may be any sensor used in the art for measuring a degree or quantitative level of UV exposure.

In addition, a PDT's battery may be charged during the sterilization treatment for efficiency and convenience in settings such as a hospital whose employees operate in shifts. For convenience then, the chamber may also be implemented with a mechanical arm or wheel that sequences a number of PTDs through the sterilizer automatically. The proportionally sized PDTs in conformity with the size of the chamber would therefore be advantageous. Alternatively, a conveyor belt could be utilized or other high throughput mechanism. If the sterilization system 200 is integrated as a high throughput system, it may be beneficial to seal the sterilization chamber 201 from potentially damaging cleansing procedures that could be performed on the PDT 202 as part of the high throughput system.

Figure 3:
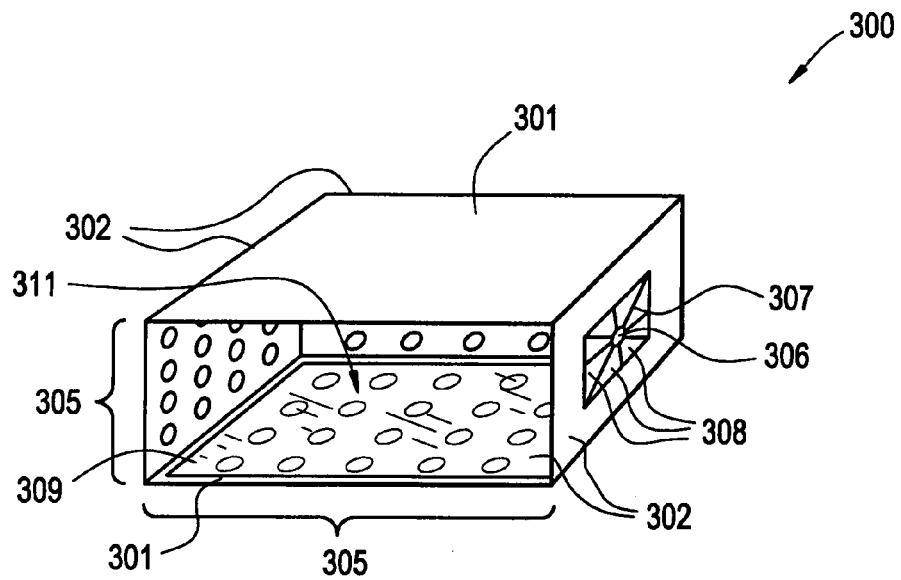
FIG. 3 is a perspective view of an embodiment of the apparatus through a side wall of the apparatus, the side wall of which is transparent for illustration purposes.

Depicted in FIG. 3 is a sterilization chamber 300 of an embodiment of the present invention. The chamber includes top and bottom walls 301 and side walls 302 (the front side wall 302 of which is transparent in FIG. 3 for illustration purposes). In one embodiment, arrays of LEDs 305 are incorporated with the each top and bottom wall 301 and each side wall 302. For exemplary purposes and not limitation, each array of LEDs 305 may form a wall 301, 302. Any number of arrays 305, however, may be assembled to comprise an individual wall 301, 302. In this view, front wall 302 is not shown in order to give visibility to the interior 311 of chamber 300. Any number of arrays 305 may be utilized, however, in sterilizing target surface areas provided that UV light will emit radiation upon each targeted surface. Chamber 300 illustrates a transparent sheet 309 positioned above the array of LEDs 305 so that a target device can be positioned on the sheet or holder 309 without allowing direct contact with the UVLEDs 305. An opening 306 allows access to the transparent sheet for positioning a target device. The opening 306 in one embodiment may be sealed by using a flexible covering 307 to enclose the interior 311 from the external environment. The covering 307 illustrated can be a partitioned sheet of synthetic material adaptable to the size of the opening 306 which permits a target device to be inserted into the interior chamber 311 via the opening 306. The covering 307 which serves as a seal 307 includes separate partitions 308 for easy insertion and removal of a PDT or other device while still allowing the aperture to be completely sealed when no object or device is in the opening 306. It is apparent, however, that any modification of the aperture as known in the art does not deviate from the intentions of the present invention. Any seal as known in the art may be included with any aperture or door that provides access to the chamber.

Figure 4:
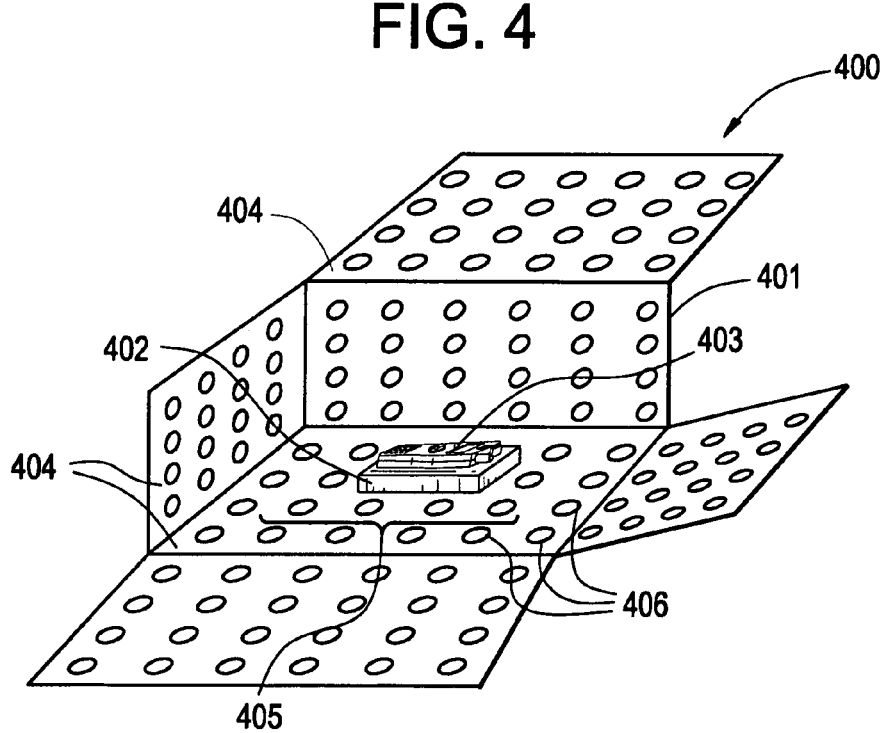
FIG. 4 is a side perspective view of another embodiment of a system.

FIG. 4 demonstrates another embodiment of a sterilization compartment 400 comprising a sterilization chamber 401. The open chamber 401 comprises multiple walls 404 which are capable of enclosing a transparent sample holder 402 of fused silica or quartz for positioning the PDT 403. The modified UV transparent holder 402 as illustrated can be a block within the interior of the chamber 400. The individual sample holder 402 may not be physically connected to the system and may also be removable with the PDT. For exemplary purposes and not limitation, the holder 402 is depicted as a transparent block 402. Any holder 402, however, that exposes substantially all surfaces of the PDT to UV radiation may be utilized. For example, a holder suspended from an upper surface of the superior top wall of the chamber would easily allow multiple surfaces and features of the PDT to be exposed to irradiating UV energy. In the system 400, then, any holder and target may be used in combination with the sterilization device. Multiple holders 402 and/or PDTs 403 may be incorporated for sterilization.

In addition, the chamber in this embodiment is assembled using arrays of LEDs 405 as the walls 404. In one aspect, each array of LEDs 405 may be comprised of a particular arrangement and number of individual LEDs 406 so that different modular units or arrays 405 may be assembled into the desired configuration. It would therefore be possible that each wall be removable or be incorporated with the chamber as a door. The walls 404 may be hinged to accommodate access to the interior and further provide convenient assembly. Furthermore, it may be apparent from this aspect of the invention to modify the design in multiple arrangements so that individual chambers 401 can be stacked upon one another or layered within one integral system 400. In another aspect, the enclosed design of the chamber may be modified as one integral one surrounding a holder and a target device, or modified to incorporate any number of surfaces so long as substantially all surfaces of a three-dimensional target device are capable of being irradiated simultaneously from various angles. Therefore, any dome-like structure may be constructed to be utilized over a UV reflective surface and where the target can be positioned upon a UV transparent material or other modified holder. Another variation of one embodiment may be constructed such that a suspended holder and PDT device can be enclosed by a dome-like covering which includes the multiple LEDs. Such modified surfaces would form an enclosed compartment surrounding a target device, allowing incident UV light to be directed upon each surface of the target device simultaneously.

FIG. 5 is an illustrative embodiment of a PDT 500 which may be placed in a sterilization chamber of the present invention. The PDT 500 is a multi-sided device easily handled and manipulated as a hand-held portable device 500, including a rechargeable and/or battery operated unit 508. A block barcode reader 501 in combination with the internal data processor elements 502 functionally operate with the radio 503 to keep continuous communication with any of the networks. The continuous user interface 504 may include a keypad 509 and a screen 510 covered by a unitary sheet 506, possibly manufactured as a unitary body 504. In one aspect, the unitary sheet includes dome switches 506 comprised of a non-pathogenic material such as those that can be incorporated into the composition of the plastic itself or alternative materials to prohibit biological growth and contamination of the device 500. In an exploded perspective view of the PDT 500, the dome switches 506 appear as a separate sheet that may be adhered to the interface 504. An integral assembly, however, may be included so that the interface 504 incorporates the unitary sheet 506 as a sealed unit. A sensor 505 included on a side surface 507 is capable of tracking the efficacy of sterilization as recorded by the measure of UV exposure.

Whether the UVLEDs are individually distributed within the chamber or arranged within a sheet to form an array, as discussed above, any number of transparent sheets may be incorporated within the chamber and alternated with sheets/arrays of LEDs so that the system can be multi-functioning and sterilize a variety of PDTs or other types of medical devices for use in operating rooms and surgical environments. Even when utilized outside of the medical profession, embodiments of the sterilization chamber may find other uses in industrial clean-room environments or in general applications where communication devices may need to be sanitized throughout the public sector.

Modifications of the present invention may also include incorporating any type of LED, particularly those being developed to accommodate other ranges of wavelengths for sterilization. As a cost effective choice, LEDs continue to be developed to improve their energy efficiency. Developments of organic light emitting diodes (OLEDs) could also be a possibility for being included in the present invention. The luminous efficiency which has led to development of organic light emitting diodes could also influence super-bright UV OLEDs to be developed for the present application.

There is set further herein: (A1) a method of sterilizing portable data devices comprising: enclosing a data device in a chamber, said chamber comprising one or more walls, a holder for positioning a portable data device, an aperture in at least one said wall and capable of being sealed, a plurality of UVLEDs distributed throughout said chamber, and a power supply providing energy to said UVLEDs; and irradiating the surfaces of said data device simultaneously with UV radiation thereby destroying biological contaminants which may be present on said data device. There is further set forth herein (A2) the method of (A1), further comprising a step of chemically cleaning said data device prior to said step of irradiating. There is further set forth herein (A3) the method of (A1), further comprising a step of chemically cleaning said data device within said chamber. There is further set forth herein (A4) the method of (A1), wherein said step of irradiating comprises a step of calculating the surface area of said data device in combination with determining a distribution of UVLEDs such that an appropriate measure of UV radiation is utilized to inactivate pathogens including bacteria, viruses, fungi, protozoans and parasitic microorganisms. There is further set forth herein (A5) the method of (A1), further comprising steps of removing said data device from said chamber, utilizing said data device in a sterile environment and repeating said steps of enclosing and irradiating without damaging physical, optical or electrical components of said data device.

As exemplified, the apparatus may include any chamber having LEDs which emit UV radiation to sterilize targeted surfaces. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

What is claimed is:

1. A method of sterilizing portable data devices comprising:
    enclosing a data device in a chamber, said chamber comprising one or more walls, a holder for positioning a portable data device, an aperture in at least one said wall and capable of being sealed, a plurality of UVLEDs distributed throughout said chamber, and a power supply providing energy to said UVLEDs; and
    irradiating surfaces of said data device simultaneously with UV radiation thereby destroying biological contaminants which may be present on said data device; and sensing UV exposure of the data device utilizing a UV sensor disposed on the data device.

2. The method of claim 1, further comprising a step of chemically cleaning said data device prior to said step of irradiating.

3. The method of claim 1, further comprising a step of chemically cleaning said data device within said chamber.

4. The method of claim 1, wherein said step of irradiating comprises a step of calculating a surface area of said data device in combination with determining a distribution of UVLEDs such that an appropriate measure of UV radiation is utilized to inactivate pathogens including bacteria, viruses, fungi, protozoans and parasitic microorganisms.

5. The method of claim 1, further comprising steps of removing said data device from said chamber, utilizing said data device in a sterile environment and repeating said steps of enclosing and irradiating without damaging physical, optical or electrical components of said data device.

6. The method of claim 1, wherein the method includes, utilizing the sensor, recording data indicating a number of decontaminations of the data device.

7. The method of claim 6, wherein the method further includes accessing a decontamination record utilizing a user interface of the data device.

8. The method of claim 1, wherein the method includes measuring a degree of radiation utilizing the sensor.

9. A system for sterilizing a portable data terminal comprising:
   a portable data terminal having a housing and plurality of features;
   a holder transmissive to UV radiation and supporting said portable data terminal; and
   one or more walls forming a closed compartment, said closed compartment for enclosing said holder in combination with said portable data terminal;
   wherein said one or more walls comprises at least a first surface integrating an array of LEDs for emitting UV radiation upon said portable data terminal and at least a second surface comprising a UV reflective material;
   wherein said at least a second surface disperses UV radiation throughout said closed compartment;
   wherein the portable data terminal includes a UV sensor for sensing UV exposure.

10. The system according to claim 9, wherein said housing and said features of said portable data terminal comprise materials non-supportive of pathogens.

11. The system according to claim 9, wherein said features comprise a continuous interface.

12. The system according to claim 11, wherein said continuous interface comprises dome switches or keypad components resistant to biological growth and UV degradation.

13. The system according to claim 9, wherein said array of LEDs comprises a combined energy of UV radiation such that emitted light sterilizes substantially all surface areas of said portable data terminal.

14. The system according to claim 9, wherein said portable data terminal includes a barcode reader and a data processor element.

15. The system according to claim 9, wherein the system includes an opening covered by a flexible covering.

16. The system according to claim 9, wherein the system is adapted to recharge the portable data terminal which it is being sterilized.

17. The system according to claim 9, wherein the portable data terminal includes a UV sensor for sensing UV exposure.

18. The system of claim 9, wherein the system is operative so that a decontamination record is provided utilizing the UV sensor, wherein the decontamination record is accessible utilizing a user interface of the portable data terminal.

* * * * *